United States Patent [19]

Mongeon

[11] 4,386,609
[45] Jun. 7, 1983

[54] ATTACHING ASSEMBLY FOR AN OSTEOTOMY SAW BLADE

[75] Inventor: Douglas R. Mongeon, Orange, Calif.

[73] Assignee: Minnesota Mining and Manufacturing Company, St. Paul, Minn.

[21] Appl. No.: 303,553

[22] Filed: Sep. 18, 1981

Related U.S. Application Data

[63] Continuation of Ser. No. 104,653, Dec. 17, 1979, abandoned.

[51] Int. Cl.³ .................................................. A61B 17/14
[52] U.S. Cl. ........................................ 128/317; 30/339; 30/348
[58] Field of Search ................ 128/317, 305, 92 E, 128/92 G; 30/348, 351, 335–339

[56] References Cited

U.S. PATENT DOCUMENTS

| | | | |
|---|---|---|---|
| 615,518 | 12/1898 | Baker et al. | 30/348 |
| 1,179,910 | 4/1916 | Greenfield | 128/317 |
| 3,633,583 | 1/1972 | Flehbein | 128/305 |
| 3,703,036 | 11/1972 | Karubian | 30/339 |
| 3,905,105 | 9/1975 | Tuke | 30/393 |
| 3,927,893 | 12/1975 | Dillon et al. | 279/75 |
| 3,943,934 | 3/1976 | Bent | 128/317 |
| 3,964,163 | 6/1976 | Russo | 30/166 R |
| 3,974,868 | 8/1976 | Derbyshire | 30/339 X |
| 3,977,289 | 8/1976 | Tuke | 83/835 |
| 3,986,512 | 10/1976 | Walliser | 128/317 |
| 4,020,555 | 5/1977 | Hedrick | 30/392 |
| 4,036,236 | 7/1977 | Rhodes | 128/317 |
| 4,137,631 | 2/1979 | Pickett et al. | 30/337 |

*Primary Examiner*—Michael H. Thaler
*Attorney, Agent, or Firm*—Cruzan Alexander; Donald M. Sell; William L. Huebsch

[57] ABSTRACT

An attaching assembly for releasably attaching an osteotomy saw blade in a drive assembly. The attaching assembly comprises a drive member including a head portion having a slot adapted to receive an end portion of blade with a larger portion of an aperture in the blade aligned with a socket in the head portion, and a projection on the blade positioned in one of a plurality of notches in the head portion communicating with the slot. A locking button mounted in the socket is movable between a locking position (to which it is biased) at which a slightly tapered locking portion of the button is in engagement with walls defining the larger portion of the aperture to lock the blade in the attaching assembly; and a release position at which a narrow portion of the button is aligned with the slot so that the blade can be slid into or out of the slot with walls of the blade defining a narrow portion of the aperture communicating with an edge of the blade sliding past the narrow portion of the button.

5 Claims, 5 Drawing Figures

ATTACHING ASSEMBLY FOR AN OSTEOTOMY SAW BLADE

This is a continuation of application Ser. No. 104,653, filed Dec. 17, 1979, now abandoned.

BACKGROUND OF THE INVENTION

The present invention relates to attaching assemblies for releasably attaching an osteotomy saw blade to a drive mechanism for reciprocating the saw blade.

Heretofore attaching assemblies for releasably attaching an osteotomy saw blade to a drive mechanism have included threadably engageable portions and have required tools for securing the portions in engagement with the saw blades. One such attaching assembly includes a drive member having a threaded projection over which an apertured end portion of a blade may be positioned, a washer which is positioned around the projection over the blade, and a nut which engages the threaded projection to secure the washer and blade to the drive member. Another such attaching assembly includes an internally threaded drive member over which an orificed end portion of the blade may be positioned, a retaining plate which is positioned over the side of the blade opposite the drive member, and a cap screw which attaches the retaining plate and blade to the drive member.

With either of these attaching assemblies, changing blades is time consuming. There is a possibility that the tool required to attach the blade or the separable parts of the assembly may be dropped and thus become contaminated or even lost during surgery, or that the required tool not easily be located when it is needed during surgery.

SUMMARY OF THE INVENTION

According to the present invention there is provided an attaching assembly for releasably attaching an osteotomy saw blade to a drive mechanism, which attaching assembly can be manually operated without the use of separate tools, and securely holds the saw blade in the holder during use of the saw.

The attaching assembly according to the present invention is for releasably attaching a plant-like saw blade which has an end portion with a through aperture between opposite major surfaces of the blade including a narrow aperture portion opening through one edge of the blade, and a larger aperture portion spaced from the edge of the blade; and which has a projection from one major side surface of the blade adjacent the aperture. The attaching assembly includes a drive member including a stem portion adapted to be reciprocated about an axis by the drive mechanism and a head portion at one end of the stem portion. The head portion has a slot defined by spaced parallel planar surfaces at right angles to the axis of the drive member, which slot opens through one side of the head portion and extends into the head portion past the axis, an axially extending socket communicating with the slot and through the end of the head portion opposite the stem portion, and a plurality of radially extending notches opening through its periphery and communicating with the slot. The slot is adapted to receive the end portion of the blade with the larger portion of the aperture in the blade aligned with the socket in the head portion, and the projection on the blade positioned in any one of the notches so that the blade projects from the drive member at a desired angle; and the attaching assembly includes a locking button mounted in the socket for movement axially of the drive member between a locking position (to which the button is biased) at which a slightly tapered locking portion of the button is in engagement with walls defining the larger aperture portion in the blade; and a release position at which a narrow portion of the button is aligned with the slot so that the blade can be slid into or out of the slot with walls of the blade defining the narrow portion of the aperture sliding past the narrow portion of the button.

BRIEF DESCRIPTION OF THE DRAWING

The present invention will further be described with reference to the accompanying drawing wherein like numbers refer to like parts throughout the several views and wherein.

DESCRIPTION OF THE PREFERRED EMBODIMENT

Figure 1:
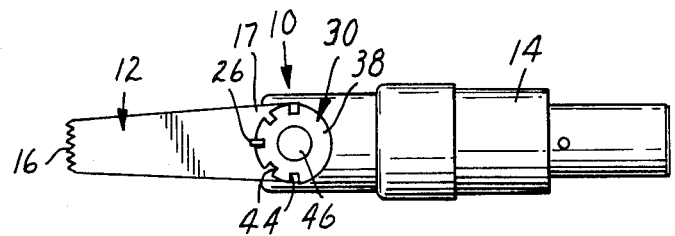
FIG. 1 is a fragmentary plan view showing an attaching assembly according to the present invention for releasably attaching an osteotomy blade to a drive assembly.

Referring now to the drawing, there is shown an attaching assembly 10 according to the present invention for releasably attaching an osteotomy blade 12 to a drive assembly 14 so that the blade 12 can be reciprocated and a plurality of teeth 16 on one end of the blade 12 can be used to sever bone. As is well known in the art, the drive assembly 14 is of a type adapted to reciprocate the blade 12 through a very small arc (e.g., 0.37 inch in length at the teeth 16) so that reciprocal motion of the teeth 16 will sever bone but will vibrate rather than cut flesh contacted by the teeth 16.

Figure 4:
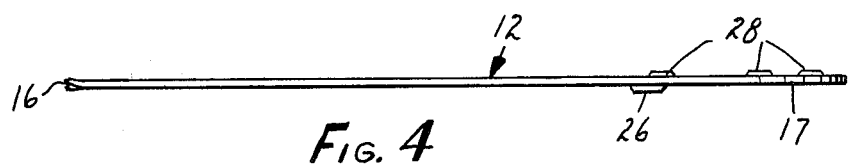
FIG. 4 is an enlarged side view of the osteotomy blade shown attached in the assembly of FIG. 1.
Figure 5:
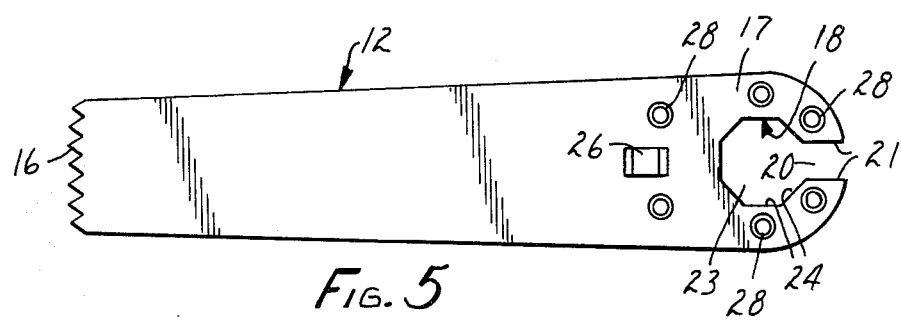
FIG. 5 is a top view of the blade of FIG. 4.

As is best seen in FIGS. 4 and 5, the blade 12 adapted to be received in the assembly 10 is elongate and plate-like with parallel major side surfaces. The blade 12 includes an end portion 17 opposite the teeth 16 having a through aperture 18 between its side surfaces including a narrow aperture portion 20 defined by spaced parallel walls 21 opening through an edge of the blade 12 opposite the teeth 16; and a larger aperture portion 23 spaced from the edge of the blade 12 and defined by octagonally disposed walls 24 as illustrated, but which alternatively could be defined by a circular wall. Also, the blade 12 has a projection 26 from one of its side surfaces located adjacent the aperture 18 centrally of the width of the blade 12 and between the aperture 18 and the teeth 16; and a plurality of dimples 28 projecting from the side surface of the blade 12 opposite the projection 26, which dimples 28 are adapted to increase the effective thickness of the blade 12 around the aperture 18. Alternatively, the entire blade could have the same thickness as the end portion 17 of the blade 12 including the dimples 28.

The attaching assembly 10 includes a drive member 30 which is generally concentric about an axis 32. The drive member 30 includes a stem portion 34 adapted to be received in bearings 36 in the drive assembly 14 (which drive assembly 14, except for the attaching assembly 10, is essentially the same as that sold by 3M Company of St. Paul, Minn., under the trade designation "D-299 Osteotomy Saw"), and is adapted to be reciprocated about its axis 32 by a drive yoke in the drive assembly 14 coupled to the drive member 30 via a drive pin 37. The drive member 30 also includes a generally cylindrical head portion 38 at one end of the stem portion 34, which head portion 38 has a slot 40 defined by spaced parallel planar surfaces at right angles to the axis 32 of the drive member 30. The slot 40 opens through one side of the head portion 38 and extends into the head portion 38 well past the axis 32. The head portion 38 also has an axially extending socket 42 communicating with the slot 40 and through the end of the head portion 38 opposite its stem portion 34, and a plurality of radially extending notches 44 on both sides of the slot 40, which notches 44 open through the periphery of the head portion 38 and communicate with the slot 40.

The slot 40 is adapted to receive the end portion 17 of the blade 12 with the larger portion 23 of the aperture 18 in the blade 12 aligned with the socket 42 in the drive member 30 and the projection 26 on the blade 12 in close-fitting engagement in any one of the notches 44 that provides a desired angle between the blade 12 and the drive member 30 or the drive assembly 14.

Figure 2:
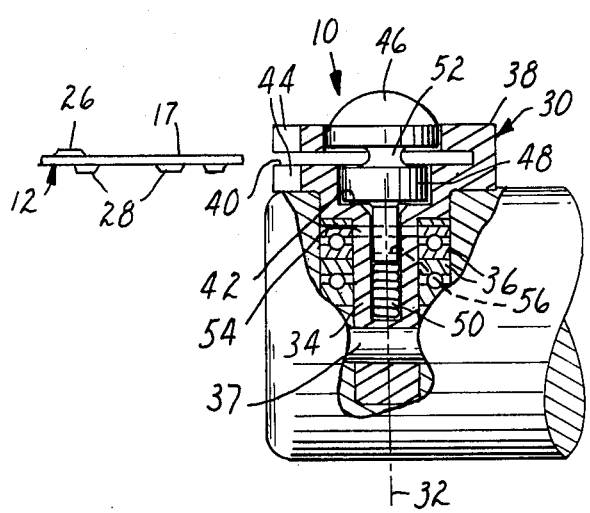
FIG. 2 is an enlarged sectional view of the attaching assembly, osteotomy blade and drive assembly of FIG. 1 shown with a locking button in the attaching assembly in a release position.
Figure 3:
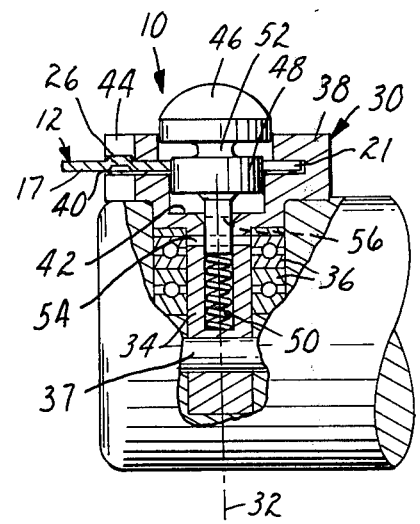
FIG. 3 is a view similar to that of FIG. 2 but shown with the locking button in a locking position.

A locking button 46 is mounted in the socket 42 for movement axially of the drive member 30 between a locking position (FIG. 3) at which a slightly tapered locking portion 48 of the locking button 46 will be in engagement with the walls 24 defining the larger portion 23 of the aperture 18 in the blade 12 (when the blade 12 is positioned in the slot 40) to releasably retain the blade 12 in the slot 40, to which locking position the button 46 is biased by a coil spring 50 between the drive member 30 and the button 46; and a release position (FIG. 2) to which the locking button 46 may be manually pressed against the bias of the spring 50 at which release position a narrow portion 52 of the locking button 48 is aligned with the slot 40. When the narrow portion 52 of the locking button 48 is aligned with the slot 40, the walls 24 defining the narrow portion 20 of the aperture 18 in the blade 12 may slide past the narrow portion 52 of the locking button 48 to afford removal or insertion of the blade 12 with respect to the drive assembly 14.

The locking button 46 is retained in the socket 42 by a retaining pin 54 extending diametrically through the socket 42 and a transverse axially elongate slot 56 in the locking button 46. The release position of the button 46 is defined by engagement of the retaining pin 54 with one end of the elongate slot 56, whereas the locking position of the button 46 is determined by engagement of the tapered locking portion 48 with the walls 24 of the aperture 18.

I claim:

1. An attaching assembly for releasably attaching a plate-like osteotomy saw blade having parallel major side surfaces to a drive mechanism for reciprocating the blade, which blade includes an end portion having a through aperture between said side surfaces including a narrow aperture portion opening through one edge of the blade and a larger aperture portion spaced from the edge of the blade, and a projection from one of the surfaces of the blade adjacent the aperture, said attaching assembly comprising:

a drive member having an axis, a stem portion adapted to be reciprocated about said axis by the drive mechanism, and a head portion at one end of said stem portion having a slot defined by spaced parallel planar surfaces at right angles to said axis opening through one side of said head portion and extending into said head portion past said axis, having an axially extending socket communicating with said slot and through the end of said head portion opposite said stem portion, and having a plurality of radially extending notches opening through its periphery and communicating with said slot, said slot being adapted to receive the end portion of a said blade with the larger aperture portion in the blade aligned with said socket in said head portion and the projection on the blade in any one of said notches so that the blade projects from the drive member at a desired angle;

a locking button mounted in said socket for movement axial of said drive member between a locking position and a release position; and means for biasing said locking button to its locking position;

said locking button having a narrow portion aligned with said slot when said button is in its release position and adapted to be received in the narrow portion of the aperture in a said blade, and a larger locking portion aligned with said slot when said button is in its locking position, said locking portion being slightly tapered so that it will be biased by said biasing means into engagement with walls defining the enlarged slot portion of the blade to releasably retain the blade in the attaching assembly.

2. An attaching assembly according to claim 1 wherein said notches are on both sides of said slot.

3. In combination:

a plate-like osteotomy saw blade having parallel major side surfaces, said blade including an end portion having walls defining a through aperture between said side surfaces including a narrow aperture portion opening through one edge of the blade and a larger aperture portion spaced from the edge of the blade and a projection from one of the side surfaces of the blade adjacent the aperture, and a plurality of teeth along the edge of the blade opposite said end portion;

a drive member having an axis, a stem portion adapted to be reciprocated about said axis by a drive mechanism, and a head portion at one end of said stem portion having a slot defined by spaced parallel planar surfaces at right angles to said axis opening through one side of said head portion and extending into said head portion past said axis, having an axially extending socket communicating with said slot and through the end of said head portion opposite said stem portion, and having a plurality of radially extending notches opening through its periphery and communicating with said slot, said slot being adapted to receive the end portion of said blade with the enlarged aperture portion in the blade aligned with said socket in said head portion and the projection on the blade in any one of said notches so that the blade projects from the drive member at a desired angle;

a locking button mounted in said socket for movement axial of said drive member between a locking position and a release position; and means for biasing said locking button to its locking position;

said locking button having a narrow portion aligned with said slot when said button is in its release position and adapted to be received in the narrow portion of said aperture in the blade, and a larger locking portion aligned with said slot when said button is in its locking position, said locking portion being slightly tapered so that it will be biased by said biasing means into engagement with the walls defining the enlarged slot portion of the blade to releasably retain the blade in the assembly.

4. A combination according to claim 3 wherein said notches are on both sides of said slot.

5. A plate-like osteotomy saw blade having parallel major side surfaces including an end portion having a through aperture between said side surfaces including a narrow aperture portion opening through one edge of the blade and a larger aperture portion spaced from the edge of the blade and a projection from one of the side surfaces of the blade adjacent the aperture, and a plurality of teeth along the edge of the blade opposite said end portion.

* * * * *

UNITED STATES PATENT AND TRADEMARK OFFICE
CERTIFICATE OF CORRECTION

PATENT NO. : 4,386,609
DATED : June 7, 1983
INVENTOR(S) : Douglas R. Mongeon

It is certified that error appears in the above—identified patent and that said Letters Patent is hereby corrected as shown below:

Col. 1, line 45, "plant-like" should read -- plate-like --.

Col. 6, lines 3-11, claim 5 should read as follows:

-- A combination according to claim 3 wherein said blade has a plurality of dimples around said aperture and projecting from the side surface of said blade opposite said projection to provide a pretermined effective thickness for the portion of the blade around said aperture. --

Signed and Sealed this

Twenty-seventh Day of March 1984

[SEAL]

Attest:

GERALD J. MOSSINGHOFF

*Attesting Officer*  *Commissioner of Patents and Trademarks*